United States Patent
Hirose et al.

(10) Patent No.: US 8,390,818 B2
(45) Date of Patent: Mar. 5, 2013

(54) OPTICAL COHERENCE TOMOGRAPHIC IMAGING APPARATUS AND OPTICAL COHERENCE TOMOGRAPHIC IMAGING METHOD

(75) Inventors: Futoshi Hirose, Yokohama (JP); Kazuro Yamada, Kawasaki (JP); Kazuhide Miyata, Yokohama (JP); Kenji Muto, Fujisawa (JP); Nobuhiro Tomatsu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 316 days.

(21) Appl. No.: 12/668,253

(22) PCT Filed: May 7, 2009

(86) PCT No.: PCT/JP2009/058957
§ 371 (c)(1),
(2), (4) Date: Jan. 8, 2010

(87) PCT Pub. No.: WO2009/136659
PCT Pub. Date: Nov. 12, 2009

(65) Prior Publication Data
US 2010/0321700 A1 Dec. 23, 2010

(30) Foreign Application Priority Data

May 8, 2008 (JP) .................................. 2008-122633
Apr. 28, 2009 (JP) .................................. 2009-109393

(51) Int. Cl.
*G01B 11/02* (2006.01)

(52) U.S. Cl. ..................................................... 356/497

(58) Field of Classification Search .................. 356/479, 356/497; 250/227.19, 227.27
See application file for complete search history.

(56) References Cited

U.S. PATENT DOCUMENTS
(Continued)

FOREIGN PATENT DOCUMENTS

| EP | 2 044 879 | 4/2009 |
|---|---|---|
| JP | 2002-174769 | 6/2002 |

(Continued)

OTHER PUBLICATIONS

Notification Concerning Transmittal of International Preliminary Report on Patentability dated Nov. 18, 2010, forwarding International Preliminary Report on Patentability dated Nov. 9, 2010, in counterpart International Application No. PCT/JP2009/058957.

*Primary Examiner* — Michael A Lyons
(74) *Attorney, Agent, or Firm* — Fitzpatrick, Cella, Harper & Scinto

(57) ABSTRACT

A beam diameter varying portion varies a first beam diameter of a measuring beam incident on an optical portion to a second beam diameter larger than the first beam diameter. An adjustment portion adjusts a condensing position of the measuring beam on the optical portion based on intensity information of a return beam from a position of an inspection object with the first beam diameter. The beam diameter is varied from the first to the second beam diameter by the beam diameter varying portion at the position adjusted by the adjustment portion to cause the measuring beam having the second beam diameter to be incident. A condensing position can be adjusted in a relatively short time because the measuring beam small in beam diameter is used, and a combined beam can be acquired with high transverse resolution because the measuring beam large in beam diameter is used.

37 Claims, 10 Drawing Sheets

U.S. PATENT DOCUMENTS

| | | | |
|---|---|---|---|
| 5,459,570 A | 10/1995 | Swanson et al. | |
| 6,307,628 B1* | 10/2001 | Lu et al. | 356/124 |
| 6,948,818 B2* | 9/2005 | Williams et al. | 351/211 |
| 7,236,251 B2 | 6/2007 | Takaoka | |
| 7,297,910 B2* | 11/2007 | Fomitchov | 250/201.2 |
| 7,450,242 B2* | 11/2008 | Toida et al. | 356/479 |
| 7,859,682 B2 | 12/2010 | Smith et al. | |
| 7,909,463 B2* | 3/2011 | Dick et al. | 351/211 |
| 2002/0048025 A1 | 4/2002 | Takaoka | |
| 2004/0036838 A1 | 2/2004 | Podoleanu et al. | |
| 2006/0066865 A1* | 3/2006 | Tsujita | 356/479 |
| 2006/0173445 A1* | 8/2006 | Bille | 606/5 |
| 2006/0187462 A1 | 8/2006 | Srinivasan et al. | |
| 2007/0188704 A1 | 8/2007 | Fukuma et al. | |
| 2008/0192236 A1 | 8/2008 | Smith et al. | |
| 2009/0091766 A1 | 4/2009 | Hirose | |
| 2009/0285354 A1 | 11/2009 | Hirose et al. | |
| 2010/0103374 A1 | 4/2010 | Hirose et al. | |

FOREIGN PATENT DOCUMENTS

| | | |
|---|---|---|
| JP | 2008-520992 A | 6/2008 |
| WO | 2006/054116 A2 | 5/2006 |

* cited by examiner

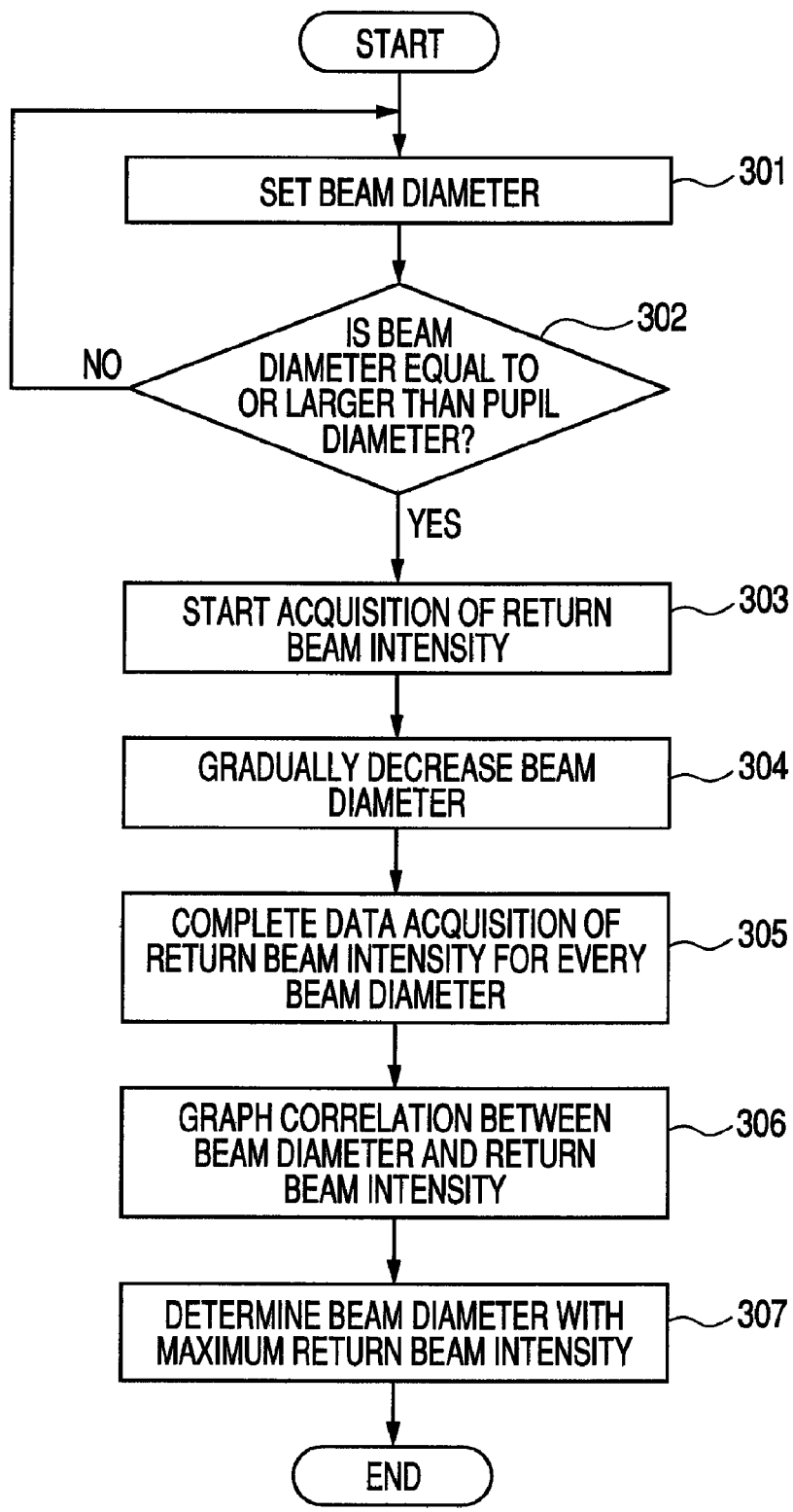

251  AP  BD

OPTICAL COHERENCE TOMOGRAPHIC IMAGING APPARATUS AND OPTICAL COHERENCE TOMOGRAPHIC IMAGING METHOD

TECHNICAL FIELD

The present invention relates an optical coherence tomographic imaging apparatus and an optical coherence tomographic imaging method. In particular, the invention relates to an optical coherent tomographic imaging apparatus and an optical coherence tomographic imaging method used in ophthalmic diagnosis and treatment.

BACKGROUND ART

Optical coherence tomography (OCT) can acquire a tomographic image of a sample with high resolution and is mainly used as an ophthalmic instrument. An apparatus using the OCT (OCT apparatus) is equipped with a coherence system and can conduct measurement with high sensitivity by irradiating an eyeground with a measuring beam (low coherent beam) and combining a return beam from the eyeground with a reference beam. At this time, the measuring beam is projected at a predetermined position of the retina to acquire a tomographic image of the eyeground.

Here, it may be difficult in some cases to project the measuring beam at the predetermined position of the retina due to factors of eyes to be inspected, such as amblyopia. At this time, it is necessary to project the measuring beam at the predetermined position of the retina by adjusting an optical system according to the optical characteristics of each eye to be inspected, and so it takes a long time to adjust the optical system.

In recent years, there has been a stronger demand for acquiring a tomographic image with high resolution by the OCT apparatus. Therefore, when a tomographic image is acquired by making a beam diameter of a measuring beam large, it takes a longer time to adjust such an optical system.

On the other hand, it is also desired to shorten the time for adjusting the optical system. In particular, shortening of the time required of imaging in the ophthalmic diagnosis of the retina is related to lightening a burden on a subject, so that it is strongly desired to shorten the time for adjusting such an optical system.

In order to meet the above two demands, an optical apparatus using OCT and optical coherence microscopy (OCM) is disclosed in Japanese Patent Application Laid-Open No. 2002-174769 (Patent Art. 1). This apparatus is so constructed that OCT is used in confirmation of a large structure in a vital sample and can be changed to OCM when a noticeable region therein is observed with minuter resolution. At this time, OCT and OCM are greatly different in depth of focus, so that the apparatus is so constructed that beam diameters can be set according to OCT having a small numerical aperture and OCM having a great numerical aperture using a beam diameter converting optical system to permit observation at a high S/N ratio.

DISCLOSURE OF THE INVENTION

The apparatus disclosed in Patent Art. 1 (Japanese Patent Application Laid-Open No. 2002-174769) can observe a noticeable region in a large structure in a vital sample confirmed with minuter resolution by OCT by changing to OCM, thereby solving a problem that it takes a long time for adjustment for projecting a measuring beam in OCM with a shallow depth of focus at a predetermined position.

However, Patent Art. 1 (Japanese Patent Application Laid-Open No. 2002-174769) does not at all consider a problem caused by making a beam diameter of a measuring beam large using the beam diameter converting optical system upon tomographic imaging with high resolution by imaging by the OCT apparatus.

In the tomographic imaging by OCT, the beam diameter of the measuring beam is made large using the beam diameter converting optical system, whereby acquiring a tomographic image with high resolution. However, when the beam diameter of the measuring beam is made large in such a manner, the depth of focus becomes shallow, so that it is difficult to project the measuring beam at a predetermined position, and it takes a long time to adjust the optical system.

It is an object of the present invention to provide an optical coherence tomographic imaging apparatus and an optical coherence tomographic imaging method, which can shorten the imaging time upon acquiring a tomographic image with high resolution by OCT, in view of the above-described problems.

The present invention provides an optical coherence tomographic imaging apparatus and an optical coherence tomographic imaging method, which are constituted as described below.

An optical coherence tomographic imaging apparatus according to the present invention is an optical coherence tomographic imaging apparatus, in which light from a light source is split into a measuring beam and a reference beam, the measuring beam is guided to an inspection object, the reference beam is guided to a reference mirror, and a return beam of the measuring beam reflected or scattered by the inspection object and the reference beam reflected by the reference mirror are used to image a tomographic image of the inspection object, the apparatus comprising a beam diameter adjusting unit for adjusting a beam diameter of the measuring beam, a return beam splitting unit for splitting the return beam into a first return beam and a second return beam, a first detection unit for detecting an intensity of the first return beam from the splitting unit, a condensing position adjusting unit for adjusting a condensing position of the measuring beam on the inspection object with the beam diameter adjusted by the beam diameter adjusting unit based on the detected intensity of the first return beam by the first detection unit, a second detection unit for detecting the intensity of a combined beam obtained by combining the second return beam from the splitting unit with the reflected beam of the reference beam reflected by the reference mirror, and an optical path length adjusting unit for adjusting an optical path length of the reference beam with the adjusted condition by the condensing position adjusting unit based on the detected intensity of the combined beam by the second detection unit.

An optical coherence tomographic imaging method according to the present invention is an optical coherence tomographic imaging method in an optical coherence tomographic imaging apparatus, in which light from a light source is split into a measuring beam and a reference beam, the measuring beam is guided to an inspection object, the reference beam is guided to a reference mirror, and a return beam of the measuring beam reflected or scattered by the inspection object and the reference beam reflected by the reference mirror are used to image a tomographic image of the inspection object, the method comprising a first step of adjusting a beam diameter of the measuring beam to a beam diameter smaller than a beam diameter upon measurement using a beam diameter adjusting unit in a preparatory stage before tomographic imaging, detecting by a first detection unit an intensity of a first return beam of first and second return beams split by a splitting unit for splitting the return beam, and adjusting a condensing unit for condensing the measuring beam on the inspection object based on the detected beam intensity, a second step of detecting by a second detection unit the intensity of a combined beam obtained by combining the second return beam split by the return beam splitting unit with the reflected beam of the reference beam reflected by the reference mirror with the position of the condensing unit adjusted in the first step, and adjusting an optical path length of the reference beam by an optical path length adjusting unit based on the detected beam intensity, a third step of adjusting the beam diameter of the measuring beam to a beam diameter larger than the beam diameter in the preparatory stage using the beam diameter adjusting unit in an imaging stage of imaging a tomographic image, detecting the intensity of the first return beam by the first detection unit, and adjusting the condensing unit for condensing the measuring beam on the inspection object based on the detected beam intensity, and a fourth step of detecting the intensity of the combined beam by the second detection unit with the adjusted condition of the condensing unit in the third step, and adjusting the optical path length of the reference beam by the optical path length adjusting unit based on the detected beam intensity.

A storage medium readable by a computer according to another embodiment of the present invention stores a program for performing the above-described optical coherence tomographic imaging method with the computer.

A program according to a further embodiment of the present invention comprises performing the above-described optical coherence tomographic imaging method with a computer.

An optical coherence tomographic information acquisition apparatus according to a still further embodiment of the present invention comprises a return beam detection portion for detecting intensity information of a return beam from an inspection object, an optical portion for irradiating an arbitrary position of the inspection object with a measuring beam applied on the inspection object, a beam diameter varying portion for varying a first beam diameter of the measuring beam incident on the optical portion to a second beam diameter larger than the first beam diameter, an adjustment portion for adjusting an irradiation position of the measuring beam in the optical portion based on the intensity information of the return beam from the arbitrary position of the inspection object in the first beam diameter, and a combined beam detection portion for detecting a combined beam of the return beam from the inspection object with a reference beam, wherein the first beam diameter is changed to the second beam diameter by the beam diameter varying portion under the condition adjusted by the adjustment portion such that the measuring beam having the second beam diameter is incident.

According to the present invention, an optical coherence tomographic imaging apparatus and an optical coherence tomographic imaging method which can shorten the imaging time upon acquiring a tomographic image with high resolution by an OCT apparatus can be realized.

Further features of the present invention will become apparent from the following description of exemplary embodiments with reference to the attached drawings.

BRIEF DESCRIPTION OF THE DRAWINGS

FIGS. 6A and 6B are flow diagrams illustrating determination of a beam diameter in Examples 3 and 4.

BEST MODE FOR CARRYING OUT THE INVENTION

Figure 1:
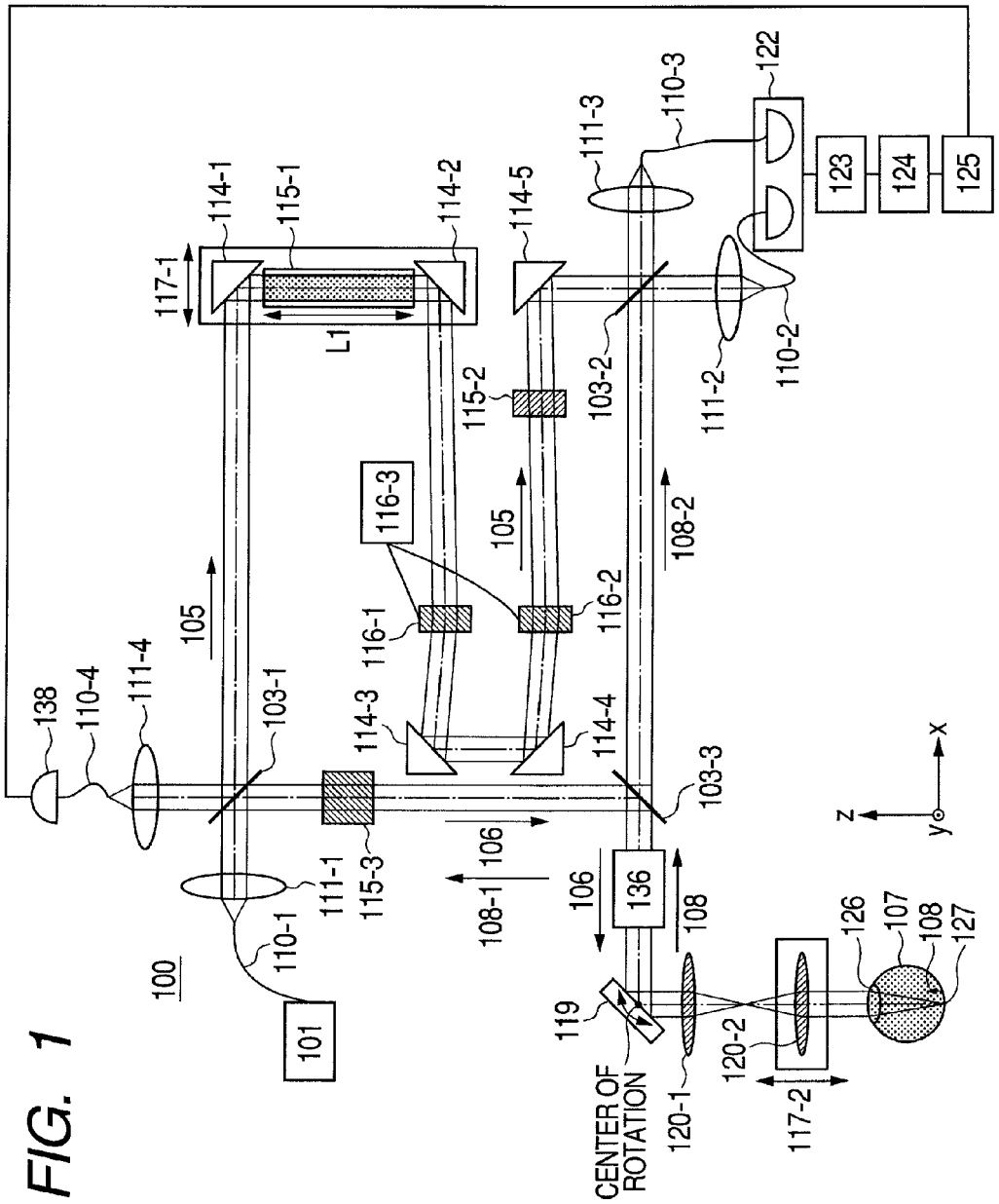
FIG. 1 illustrates the schematic construction of the whole optical system of an OCT apparatus in Example 1 of the present invention.

Improvements in resolution and contrast and shortening of an imaging time can be achieved in tomographic imaging by OCT, in particular, tomographic imaging of the retina in an eyeground of an eye to be inspected.

When the beam diameter of the measuring beam is made large as described above, there is a problem that the depth of focus becomes shallow, and so focusing is difficult because it takes a long time for the focusing. There is also a problem that it is difficult to project a measuring beam at a predetermined position due to the optical characteristics of each eye to be inspected, and so contrast is lowered.

The present inventors have found that these problems are solved by the following constitution. The outline thereof is described. In a preparatory stage for tomographic imaging, the beam diameter of the measuring beam is made smaller than a beam diameter upon an imaging stage, whereby a focusing range capable of roughly acquiring a tomographic image with deep depth of focus is obtained by adjusting the optical path length of a reference beam by an optical path length adjusting unit.

The position (focusing range) of the optical path length of the reference beam adjusted by the optical path length adjusting unit is recorded.

On the other hand, in an imaging step for imaging a tomographic image, the beam diameter of the measuring beam is made larger than the beam diameter in the preparatory stage before imaging to acquire an image with high resolution.

At this time, the depth of focus becomes shallow. However, it is easy to make adjustment to a focusing position upon projecting the measuring beam at a predetermined position by using the adjusted position (focusing range) of the optical path length of the reference beam recorded above as a reference, and so the imaging time can be shortened.

In the imaging stage, the beam diameter of the measuring beam is gradually varied, and the intensity of a return beam is measured, whereby the beam diameter of the measuring beam can be adjusted to a beam diameter at which the return beam intensity becomes maximum, and the contrast can be improved.

In the imaging stage, the beam form or beam incidence position of the measuring beam is varied, whereby the contrast can be more improved.

Such an OCT apparatus as described above can be constructed in the following manner in an embodiment of the present invention.

In the OCT apparatus according to this embodiment, an optical coherence tomographic imaging apparatus, in which light from a light source is split into a measuring beam and a reference beam, the measuring beam is guided to an inspection object, the reference beam is guided to a reference mirror, and a return beam of the measuring beam reflected or scattered by the inspection object and the reference beam reflected by the reference mirror are used to image a tomographic image of the inspection object, is equipped with a beam diameter adjusting unit for adjusting a beam diameter of the measuring beam.

This beam diameter adjusting unit is provided in an optical path for guiding the measuring beam to the inspection object and is constructed by an expandable optical system. For example, this unit can be constructed as a variable beam expander 136 arranged in the optical path of the measuring beam in the OCT apparatus illustrated in FIG. 1.

The OCT apparatus is also equipped with a return beam splitting unit for splitting the return beam into a first return beam and a second return beam.

For example, this splitting unit can be constructed as a beam splitter 103-3 arranged in the optical path of the measuring beam in the OCT apparatus illustrated in FIG. 1.

The OCT apparatus is further equipped with a first detection unit for detecting the intensity of the first return beam from the splitting unit.

For example, this first detection unit can be constructed as a detector 138, to which the first return beam is guided, in the OCT apparatus illustrated in FIG. 1.

The OCT apparatus is still further equipped with a condensing position adjusting unit for adjusting a position of a condensing unit for condensing the measuring beam on the inspection object with the beam diameter adjusted by the beam diameter adjusting unit based on the first return beam intensity detected by the first detection unit.

For example, this condensing position adjusting unit for the condensing unit can be constructed as an electric stage 117-2 in the OCT apparatus illustrated in FIG. 1.

The OCT apparatus is yet still further equipped with a second detection unit for detecting the intensity of a combined beam obtained by combining the second return beam from the splitting unit with the reflected beam of the reference beam reflected by the reference mirror.

For example, this second detection unit can be constructed as a balanced detector 122 in the OCT apparatus illustrated in FIG. 1.

The OCT apparatus is yet still further equipped with an optical path length adjusting unit for adjusting the optical path length of the reference beam with the position of the condensing unit adjusted by the condensing position adjusting unit based on the combined beam intensity detected by the second detection unit.

For example, this optical path length adjusting unit can be constructed as an electric stage 117-1 in the OCT apparatus illustrated in FIG. 1.

The OCT apparatus can also be constructed so as to have a unit for recording the position of the optical path length of the reference beam adjusted by the optical path length adjusting unit.

Upon execution of an optical coherence tomographic imaging method using the OCT apparatus in this embodiment, optical tomographic imaging can be conducted through the following steps.

In a preparatory stage for tomographic imaging, which is a first step, the beam diameter of the measuring beam is adjusted to a beam diameter smaller than a beam diameter upon measurement using the beam diameter adjusting unit, the intensity of the first return beam of the first and second return beams split by a return beam splitting unit is detecting by the first detection unit, and the position of the condensing unit for condensing the measuring beam on the inspection object is adjusted based on the beam intensity detected.

In a second step, the intensity of a combined beam obtained by combining the second return beam split by the return beam splitting unit with the reflected beam of the reference beam reflected by the reference mirror is detected by the second detection unit with the position of the condensing unit adjusted in the first step, and the optical path length of the reference beam is adjusted by the optical path length adjusting unit based on the beam intensity detected.

In this manner, in the preparatory stage before tomographic imaging, a focusing range capable of roughly acquiring a tomographic image with deep depth of focus by the measuring beam made small in beam diameter is obtained by adjusting the optical path length of the reference beam by the optical path length adjusting unit, whereby the focusing range can be obtained without requiring a time. At this time, the position (focusing range) of the optical path length of the reference beam adjusted by the optical path length adjusting unit is recorded.

In an imaging stage of imaging a tomographic image, which is a third step, the beam diameter of the measuring beam is adjusted to a beam diameter larger than the beam diameter in the preparatory stage using the beam diameter adjusting unit, the intensity of the first return beam is detected by the first detection unit, and the position of the condensing unit for condensing the measuring beam on the inspection object is adjusted based on the beam intensity detected.

In a fourth step, the intensity of the combined beam is detecting by the second detection unit with the position of the condensing unit adjusted in the third step by using, for example, the recorded position of the optical path length adjusted by the optical path length adjusting unit as a reference, and the optical path length of the reference beam is adjusted by the optical path length adjusting unit based on the beam intensity detected.

As described above, upon tomographic imaging, the optical path length of the reference beam can be quickly adjusted by using the recorded position of the optical path length adjusted by the optical path length adjusting unit as a reference, for example, using the vicinity of a center of the position adjusted by the optical path length adjusting unit as a reference.

In this embodiment, the apparatus may also be constructed so as to have a unit for reporting that the first or second return beam does not get at an intensity necessary to be detected by the first or second detection unit.

By providing this unit, it is possible to take proper measures when the intensity of the return beam does not reach a predetermined intensity.

In this embodiment, at least one optical path of an optical path to guide the light from the light source to an optical path at which it is split into the measuring beam and the reference beam, an optical path to guide the measuring beam to an inspection object and an optical path to guide the reference beam to the reference mirror may be constructed by an optical fiber.

By this construction, a small-sized and cheap OCT apparatus can be realized. In this embodiment, at least one step of the first to fourth steps may be constituted so as to be automatically conducted.

In another embodiment, the optical coherence tomographic imaging method according to the above-described embodiment may also be stored, as a program for having it executed by a computer, in a storage medium (for example, flexible disc, hard disc, optical disc, magneto-optical disc, CD-ROM, CD-R, magnetic tape, non-volatile memory card, ROM, EEPROM or Blu-ray disc) readable by the computer.

In a further embodiment, a program for performing the above-described optical coherence tomographic imaging method with a computer may be provided.

(Optical Coherence Tomographic Information Acquisition Apparatus)

Figure 7A:
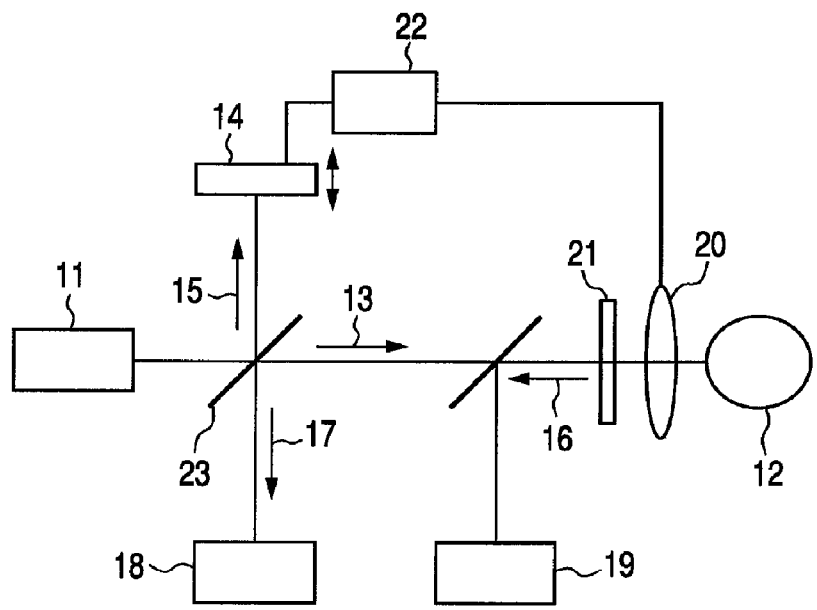
FIGS. 7A, 7B and 7C typically illustrate an optical coherence tomographic information acquisition apparatus according to an embodiment of the present invention.

The optical coherence tomographic information acquisition apparatus according to another embodiment of the present invention will be described with reference to FIGS. 7A to 7C.

First, a return beam detection portion 19 detects the intensity information of a return beam 16 from an inspection object (for example, an eyeground) 12. The return beam detection portion 19, which can detect the intensity of the beam, is, for example, a photo diode and photomultiplier.

Then, an optical portion 20 irradiates an arbitrary position (irradiation position) of the inspection object 12 with a measuring beam 13 incident on the inspection object 12. The optical portion 20 may condense the beam incident on the optical portion 20 to the above-described position and is, for example, a lens.

A beam diameter varying portion 21 varies the first beam diameter 25 of the measuring beam 13 incident on the optical portion 20 to a second beam diameter 26 larger than the first beam diameter 25. The beam diameter varying portion 21 may vary the size of the beam diameter of the beam incident on the beam diameter varying portion 21. Examples thereof include a variable beam expander (typically, such a construction that a beam diameter can be varied while keeping a substantially parallel beam using an optical system such as a lens). However, this portion is not limited thereto, and it may be such a construction (for example, variable aperture) that the size of a bore irradiated with the beam can be varied.

Figure 7B:
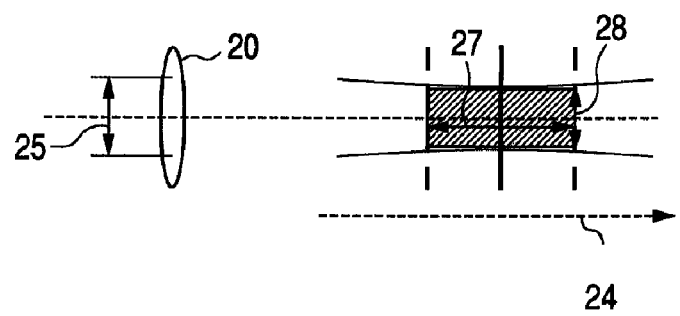
Figure 7C:
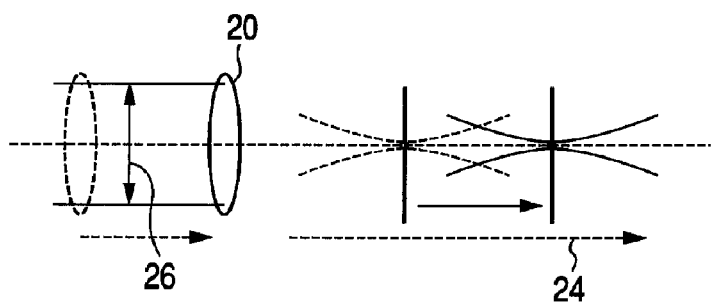

In the case of the first beam diameter 25, the spot diameter at the irradiation position is large (FIG. 7B). At this time, the depth of focus 27 is deep, and transverse resolution 28 (resolution in a direction perpendicular to the direction of the optical axis) is low. In the case of the second beam diameter 26, the spot diameter at the irradiation position is small (FIG. 7C). At this time, the depth of focus is shallow, and the transverse resolution is high.

An adjustment portion 22 is an adjustment portion for adjusting a position of the beam applied by the optical portion 20 in the inspection object 12 substantially in the direction of the optical axis (or the depth direction of the inspection object) based on the intensity information of the return beam (or using the intensity information of the return beam) from the arbitrary position of the inspection object 12 in the first beam diameter 25. The adjustment portion 22 desirably adjusts the position of the optical portion 20 in the direction of the optical axis. Otherwise, the apparatus may be moved with respect to the inspection object 12. The adjustment portion 22 is desirably so constructed that the difference between the optical path length of the measuring beam 13 and the optical path length of a reference beam 15 is adjusted. By this construction, a coherence gate (position where the length of the path of the measuring beam and the length of the path of the reference beam are substantially the same) can be adjusted. The adjustment by the adjustment portion 22 may be conducted with the inspection object being irradiated with the measuring beam of the second beam diameter.

A combined beam detection portion 18 detects a combined beam 17 (or a coherence beam) of the return beam 16 from the inspection object 12 and the reference beam 15. The combined beam detection portion 18, which can detect the intensity of the beam, is a photo diode and photomultiplier, for example. The detection portion may also be so constructed (balanced detector) that two photo diode are used to electrically remove thermal noise (FIG. 1).

The optical coherence tomographic information acquisition apparatus is so constructed that the beam diameter is varied from the first beam diameter 25 to the second beam diameter 26 by the beam diameter varying portion 21 at the position adjusted by the adjustment portion 22 in such a manner that the measuring beam having the second beam diameter 26 is incident.

By this construction, the focal position (focus) can be adjusted in a relatively short period of time because the measuring beam small in beam diameter is used, and the combined beam can be acquired with high transverse resolution because the measuring beam large in beam diameter is used.

The optical coherence tomographic information acquisition apparatus according to this embodiment typically has the following.

First, a light source 11 is provided. The light source 11, which is a low coherent light source, is, for example, SLD (super luminescent diode).

Then, a splitting portion (splitting unit) 23 for splitting light from a light source 11 into the measuring beam 13 incident on the inspection object 12 and the reference beam 15 incident on a reference portion 14 is provided. This splitting portion is also a combining portion for combining the return beam 16 from the inspection object 12 with the reference beam 15 reflected by the reference portion 14. An optical system commonly using the splitting portion and the combining portion (Michelson interferometer; construction in FIG. 7A) as described above may be used. However, an optical system separately using the splitting portion and the combining portion (Mach-Zehnder interferometer; FIG. 1) may also be used.

At this time, it is desirably so constructed that intensity information as to the tomographic position of the inspection object in the optical axis direction of the optical system is acquired. Needless to say, the optical coherence tomographic imaging apparatus according to the present invention is not limited thereto.

(Beam Condition Varying Portion)

Here, there is a problem that it takes a long time for acquiring a tomographic image having high contrast due to the optical characteristics (mainly, aberration such as astigmatism) of individual eyes to be inspected. The apparatus desirably has the following construction for solving this problem. However, the present invention is not limited thereto.

The apparatus is desirably equipped with a beam condition varying portion (for example, '236' in FIGS. 8A and 8B) for varying the beam condition of the measuring beam 13 having the second beam diameter 26. The beam condition is at least one of the form, the size and the position in the in-plane direction substantially perpendicular to the direction of the optical axis of the measuring beam. However, the condition is not limited thereto and may be any beam condition.

The beam condition varying portion is desirably constructed by containing a plurality of lenses for forming the beam condition of the measuring beam by incidence of the measuring beam. The beam condition varying portion is also desirably so constructed that among the plural lenses the beam condition at the time of incidence of the measuring beam to a first lens and the beam condition at the time of incidence of the measuring beam to a second lens are different from each other.

The beam condition varying portion is desirably equipped with a disc (for example, '251' in FIGS. 8B and 8C) arranged perpendicularly to the optical axis direction and a plurality of openings (for example, FIGS. 9A to 9L) provided in the disc. This portion is desirably so constructed that the measuring beam is selectively incident on any of the openings by rotating the disc.

The intensity information of the return beam is detected for every beam condition varied by the beam condition varying portion. The combined beam obtained by using the measuring beam having the beam condition selected based on the detected intensity information is detected by the combined beam detection portion.

A tomographic image having high contract can be thereby acquired in a short period of time irrespective of the optical characteristics (mainly, aberration such as astigmatism) of individual eyes to be inspected.

The above-described matter will be described in detail in Example 4.

EXAMPLES

The present invention will hereinafter be described by Examples.

Example 1

An OCT apparatus (or optical coherence tomographic information acquisition apparatus) in Example 1 is described. In this Example, TD-OCT (time domain OCT) for acquiring a tomographic image of a retina in particular is described.

However, the present invention is not limited to such TD-OCT, and it goes without saying that the present invention may also be applied to FD-OCT (fourier domain OCT).

First, the schematic construction of the optical system of the OCT apparatus in this Example is described.

FIG. 1 illustrates the schematic construction of the whole optical system of the OCT apparatus in this Example. In FIG. 1, an OCT apparatus 100 and an eye (or inspection object) 107 measured by the OCT apparatus 100 are illustrated.

The OCT apparatus is constructed by the following element: a light source 101, beam splitters 103-1 to 103-3, single mode fibers 110-1 to 110-4, lenses 111-1 to 111-4, and 120-1 and 120-2, mirrors 114-1 to 114-5, dispersion compensation glasses 115-1 to 115-3, acoustooptic modulators 116-1 and 116-2, a controller 116-3 for the acoustooptic modulators, electric stages 117-1 and 117-2, an XY scanner 119, a balanced detector 122, an amplifier 123, a filter 124, a personal computer 125, a variable beam expander 136, and a detector 138.

In this apparatus, the personal computer 125 operates as a control portion for the electric stages 117-1 and 117-2, XY scanner 119 and variable beam expander 136. The electric stages 117-1 and 117-2 adjust the rectilinear movement of the electric stages 117-1 and 117-2, the XY scanner 119 adjusts the scanning of a scanner mirror, and the variable beam expander 136 adjusts intervals between lenses.

A reference beam 105, a measuring beam 106 and return beams 108, 108-1 and 108-2 are also illustrated in FIG. 1.

A cornea 126 and a retina 127 are further illustrated therein.

As illustrated in FIG. 1, the OCT apparatus 100 of this Example forms a Mach-Zehnder interference system as a whole.

In this drawing, light outputted from the light source 101 is split into the reference beam 105 and the measuring beam 106 by the beam splitter 103-1.

The measuring beam 106 is returned as the return beam 108 reflected or scattered by the eye 107 that is an object of observation and split into the return beam (first return beam) 108-1 and the return beam (second return beam) 108-2 by the beam splitter 103-3. The return beam 108-2 of these return beams is combined with the reference beam 105 by the beam splitter 103-2.

After the reference beam 105 and return beam 108-2 are combined and split by the beam splitter 103-2, and the combined beam caused to be incident on the balanced detector 122.

The balanced detector 122 converts beam intensity to voltage, and a tomographic image of the eye 107 is formed by using a signal thereof.

The light source 101 will now be described.

The light source 101 is SLD (super luminescent diode) that is a typical low coherent light source.

The wavelength thereof is 830 nm, and the band width is 50 nm. The band width affects the resolution in an optical axis direction of the resulting tomographic image and is hence an important parameter.

In this Example, SLD has been selected as the light source. However, ASE (amplified spontaneous emission) may also be used so far as it can output low coherent light.

In view of the measurement for the eyes, a wavelength in the range of near infrared rays is proper. The wavelength affects the resolution in a transverse direction of the resulting tomographic image and is desirably a short wavelength. In this Example, 830 nm is used.

Another wavelength may also be selected according to a measuring site of the object to be observed.

The light outputted from the light source 101 is guided to the lens 111-1 through the single mode fiber 110-1 and adjusted so as to give a parallel beam having a beam diameter of 4 mm.

The optical path of the reference beam 105 will now be described.

The reference beam 105 split by the beam splitter 103-1 is caused to be continuously incident on the reference mirrors 114-1 to 114-5 to change its direction, thereby causing it to be incident on the balanced detector 122 by the beam splitter 103-2.

The dispersion compensation glasses 115-1 and 115-2 are arranged in the optical path, and the length of the dispersion compensation glass 115-1 is L1 and desirably equal to twice as much as the length (diameter) of the depth of a general eye. The dispersion compensation glass 115-1 compensates the dispersion when the measuring beam 106 goes to and comes back from the eye 107 with respect to the reference beam 105.

In this Example, the length is set to L1=46 mm, twice as much as 23 mm, to be an average diameter of a Japanese eyeball.

The electric stage 117-1 is further arranged, which can be moved in directions illustrated by the arrow and can adjust and control the optical path length of the reference beam 105.

The modulation method of the reference beam 105 will now be described.

Two acoustooptic modulators 116-1 and 116-2 are used as shifters for the frequency of the beam.

The shift frequencies of the acoustooptic modulators 116-1 and 116-2 are +41 MHz and −40 MHz, respectively. As a result, the frequency of the reference beam 105 is shifted by 1 MHz.

The dispersion compensation glass 115-2 conducts dispersion compensation for the lenses 120-1 and 120-2 used in scanning of the eye 107.

The optical path of the measuring beam 106 will now be described.

The measuring beam 106 split by the beam splitter 103-1 passes through the dispersion compensation glass 115-3, is reflected by the beam splitter 103-3 and caused to be incident on the variable beam expander 136.

The dispersion compensation glass 115-3 compensates dispersion of the acoustooptic modulators 116-1 and 116-2.

The variable beam expander 136 has a role of varying the beam diameter of the measuring beam 106. For example, the beam diameter of 4 mm can be varied between 1 mm and 8 mm.

Figure 5A:
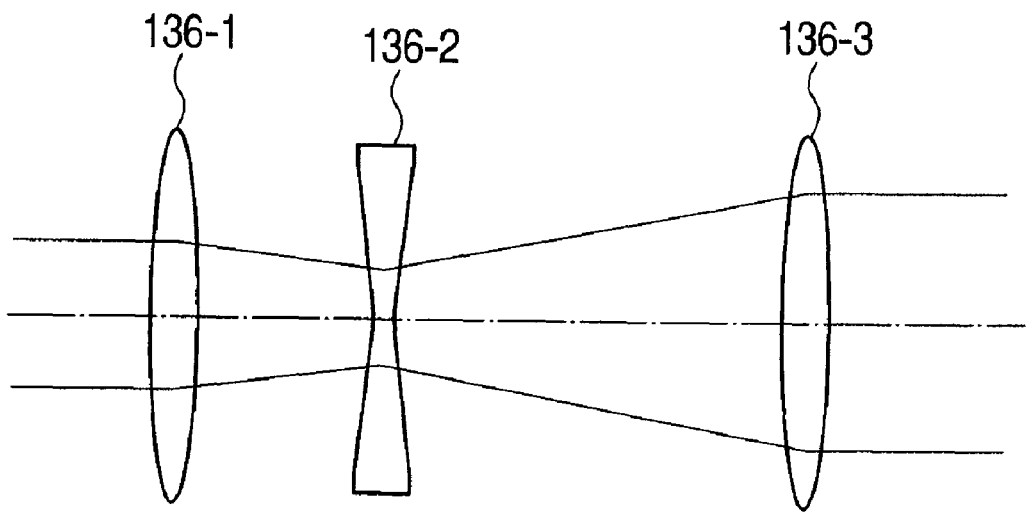
FIGS. 5A and 5B illustrate adjustment of a beam diameter using a variable beam expander in Example 1 of the present invention.
Figure 5B:
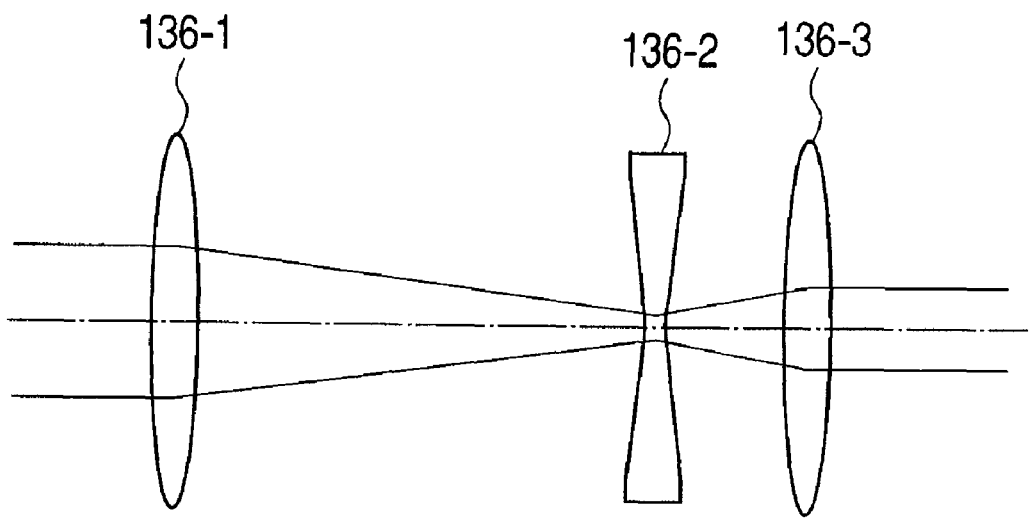

The variable beam expander 136 is constructed by, for example, containing a lens having positive refracting ability (for example, convex lenses) and a lens having negative refracting ability (for example, a concave lens) as illustrating in FIGS. 5A and 5B. Incidentally, the refracting ability means a physical quantity defined by the inverse number of a focal distance of a lens.

The position of the lens 136-2 having negative refracting ability is changed between the lenses 136-1 and 136-3 having positive refracting ability. The beam passes through the lens 136-1, is transmitted through the lens 136-2 and passes through the lens 136-3. At this time, when the lens 136-2 is positioned on the side of the lens 136-1, the beam diameter can be made large (FIG. 5A). When the lens 136-2 is positioned on the side of the lens 136-1 on the other hand, the beam diameter can be made small (FIG. 5B).

The measuring beam 106 is then caused to be incident on a minor of the XY scanner 119. The XY scanner 119 has been described as one minor herein for the sake of simplicity. In the XY scanner 119, however, two minors of an X scanning minor and a Y scanning minor are actually arranged in close vicinity to each other to conduct raster-scan on the retina 127 in a direction perpendicular to the optical axis. The center of the measuring beam 106 is adjusted so as to conform to a center of rotation of the mirror in the XY scanner 119.

The lenses 120-1 and 120-2 are of an optical system for scanning the retina 127 and have a role of scanning the retina 127 with the vicinity of the cornea 126 used as a fulcrum.

In this Example, the focal distances of the lenses 120-1 and 120-2 are 50 mm and 50 mm, respectively. When the measuring beam 106 is incident on the eye 107, it becomes the return beam 108 by reflection or scattering from the retina 127.

The return beam 108 is further split into a return beam (first return beam) 108-1 and a return beam (second return beam) 108-2 by the beam splitter 103-3, and the return beam 108-1, one of the return beams, is transmitted through the beam splitter 103-1 and guided to the detector 138.

As the detector 138, is used, for example, APD (avalanche photo diode) that is a high-speed and high-sensitivity optical sensor.

The other return beam 108-2 is guided to the balanced detector 122.

The electric stage 117-2 is further arranged, which can be moved in directions illustrated by the arrow and can adjust and control the position of the lens 120-2 attached thereto.

The lens 120-2 condenses the measuring beam on the retina 127 by adjusting the position thereof by means of the electric stage 117-2 even if the eye 107 of the subject has ametropia, which enables acquiring of a tomographic image by the OCT apparatus 100.

Although the lens 120-2 is used for adjusting the condensation position of the measuring beam 106 on the retina 127, a spherical surface mirror can be also used instead of the lens. It is also possible to conduct such adjustment by moving the eye 107 itself.

The construction of the measuring system in the OCT apparatus in this Example will now be described.

The OCT apparatus 100 can acquire a tomographic image (OCT image) formed from the intensity of interference signals by the Mach-Zehnder interference system.

The measuring system thereof is described. The return beam 108 that is a beam reflected or scattered by the retina 127 is split into the return beam 108-1 and the return beam 108-2 by the beam splitter 103-3. The return beam 108-2 of these split return beams is further split by the beam splitter 103-2. On the other hand, the reference beam 105 is also split by the beam splitter 103-2. The reference beam 105 and the return beam 108-2 are adjusted so as to be combined after the beam splitter 103-2.

The combined beam is then condensed by the lenses 111-2 and 111-3 and guided to the balanced detector 122 through the optical fibers 110-2 and 110-3, and the intensity of the combined beam of the reference beam 105 and the return beam 108-2 is converted to voltage.

The resultant voltage signal is amplified by the amplifier 123, a necessary frequency component is taken out through the filter 124, and demodulation and data processing are conducted by the personal computer 125 to form a tomographic image.

Here, the frequency of the reference beam 105 is shifted by 1 MHz as described above. Therefore, the voltage signal obtained above becomes a beat signal of 1 MHz. The return beam 108-2 is generally weak, while the reference beam 105 is strong, so that detection sensitivity can be increased.

In this Example, a band-pass filter of 1 MHz is used as the filter 124, and excessive frequency components are cut, thereby detecting the beat signal with high sensitivity.

The other one return beam 108-1 split by the beam splitter 103-3 as described above passes through the beam splitter 103-1, condensed by the lens 111-4 and guided to the detector 138 through the optical fiber 110-4.

The detector 138 is electrically connected to the personal computer 125 to enables recording and displaying the intensity of the return beam 108-1. The signal obtained by the detector 138 is an intensity signal of the return beam 108-1 by the reflection or scattering on the retina 127, and this signal does not have high depth resolution unlike the interference signal.

The adjusting method before acquiring tomographic images, which is a feature of the present invention, will now be described specifically with reference to FIG. 1 and FIGS. 2A to 2D.

FIGS. 2A to 2D are drawings for explaining the adjusting method before acquiring tomographic images and illustrate an optical system portion for causing the measuring beam to be incident on a human eye. The same elements as in FIG. 1 are given the same reference sign. When the retina of an eyeground is generally observed, the measuring beam is scanned on the retina from the viewpoint of safety to conduct observation. In this Example, observation is actually conducted while the measuring beam is scanned on the retina.

In the adjusting method of this Example, the following steps are conducted, for example, continuously. Alternatively, one may go back to some step to conduct such step, or the following steps may be automatically conducted by using a computer.

Figure 2A:
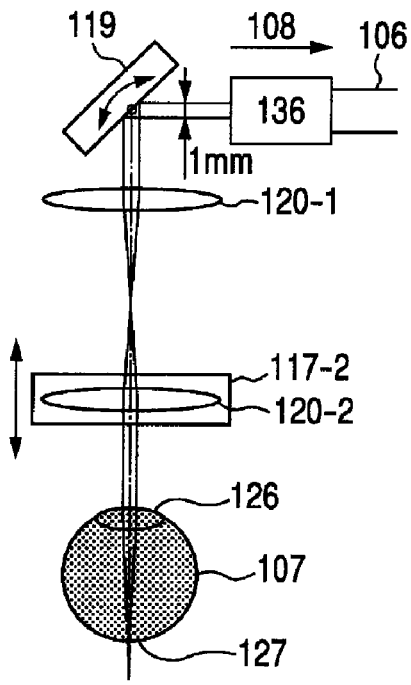
FIGS. 2A, 2B, 2C and 2D illustrate an adjusting method of the OCT apparatus in Example 1 of the present invention.

First, in a first step, the variable beam expander 136 is adjusted to adjust the beam diameter of the measuring beam 106 to 1 mm (FIG. 2A).

Then, in a second step, the electric stage 117-2 is used to adjust the position of the lens 120-2 so as to focus the measuring beam 106 on the retina 127.

The adjustment is conducted for detecting the return beam 108-1 of the measuring beam 106 from the retina 127 by the detector 138 so as to make the intensity of the return beam 108-1 substantially maximum (FIG. 1).

Since this intensity is information depending on the position of the retina, the intensity may be displayed as a graph or a two-dimensional image.

Figure 2B:
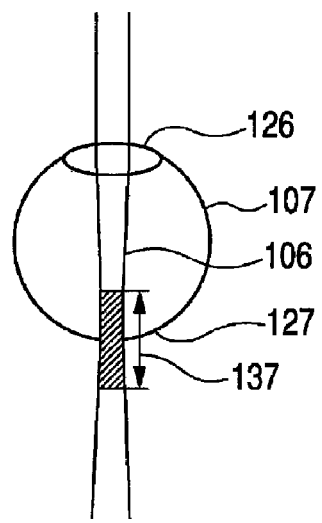

Since the beam diameter is 1 mm herein as illustrated in FIG. 2B, a focusing range 137 is about 2 mm.

Then, in a third step, the electric stage 117-1 is used to adjust the positions of the mirrors 114-1 and 114-2, thereby adjusting the optical path length of the reference beam 105 to cause the reference beam 105 and the return beam 108-2 to optically interfere with each other.

This adjustment is conducted for detecting the signal intensity of the optical interference by the balanced detector 122 so as to make the intensity maximum (FIG. 1).

Since this signal intensity is information depending on the position of the retina, the intensity may be displayed as a graph or a two-dimensional image. The position of the electric stage 117-1 herein is recorded.

Figure 2C:
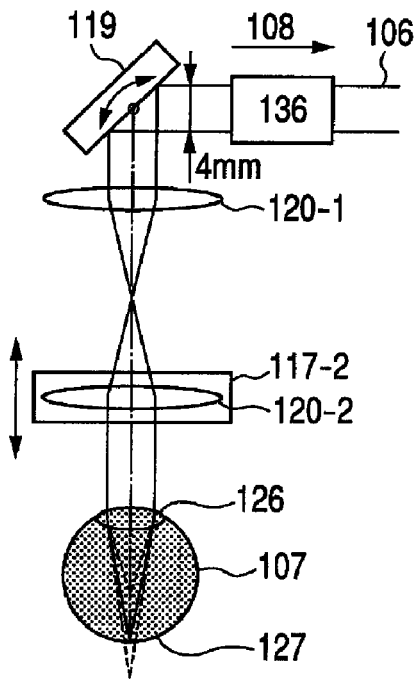

Then, in a fourth step, the variable beam expander 136 is adjusted to adjust the beam diameter of the measuring beam 106 to 4 mm (FIG. 2C). Here, the broken line and the solid line in the drawing indicate a non-focused state and a focused state, respectively (FIG. 2A).

Then, in a fifth step, the electric stage 117-2 is used to adjust the position of the lens 120-2 so as to focus the measuring beam 106 on the retina 127.

Figure 2D:
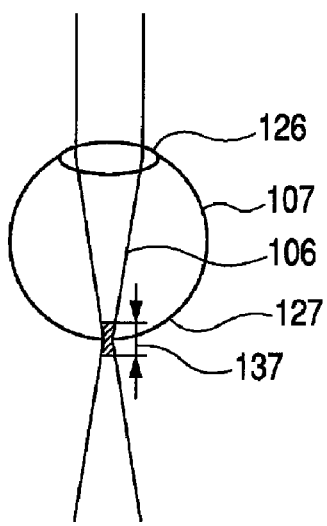

This adjusting method is the same as in the second step. Since the beam diameter is 4 mm herein as illustrated in FIG. 2D, the focusing range 137 is about 100 μm and is smaller than that in the second step.

Then, in a sixth step, the electric stage 117-1 is used to adjust the positions of the mirrors 114-1 and 114-2, thereby adjusting the optical path length of the reference beam 105 to cause the reference beam 105 and the return beam 108-2 to optically interfere with each other.

The position of the electric stage 117-1 herein is adjusted in the vicinity of the position recorded in the third step.

The method for acquiring a tomographic image using the OCT apparatus of this Example will now be described. The OCT apparatus 100 is capable of acquiring a tomographic image of a desired site of the retina 127 by controlling the electric stage 117-1 and the XY scanner 119 (FIG. 1).

The method for acquiring the tomographic image (plane parallel to the optical axis) of the retina 127 is described with reference to FIGS. 3A to 3C.

Figure 3A:
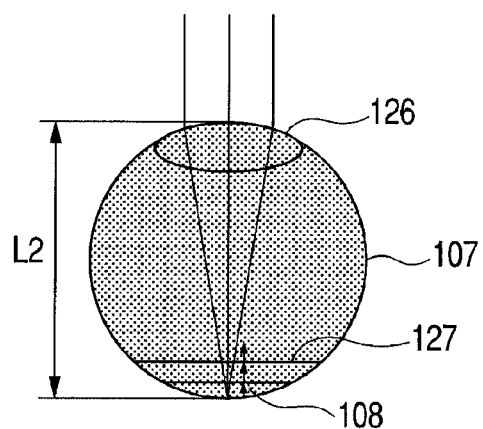
FIGS. 3A, 3B and 3C illustrate a method for acquiring an image with the OCT apparatus in Example 1 of the present invention.

FIG. 3A is a typical drawing of an eye 107 illustrating a condition of being observed by the OCT apparatus.

When the measuring beam 106 is incident on the retina 127 through the cornea 126 as illustrated in FIG. 3A, it becomes the return beam 108 by reflection or scattering at various positions, and the return beam 108 reaches the balanced detector 122 with time delays for the respective positions.

At this time, an interference signal can be detected by the balanced detector 122 only when the optical path length of the reference beam path is almost equal to the optical path length of the measuring beam path, since the band width of the light source 101 is wide, and the coherence length is short.

As described above, the frequency of the reference beam 105 is shifted by 1 MHz with respect to the measuring beam 106, and so the interference signal becomes a beat signal of 1 MHz.

Figure 3B:
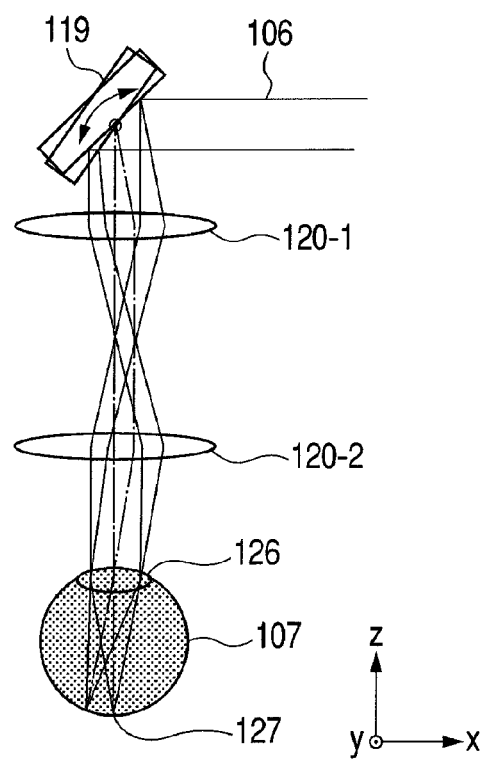

When the interference signal is detected while driving the X axis of the XY scanner 119 as illustrated in FIG. 3B, the interference signal becomes a signal having position information of the X axis.

The amplitude of this signal is squared and demodulated, thereby obtaining an intensity distribution in the X axis direction at an arbitrary XY plane of the return beam 108.

Figure 3C:
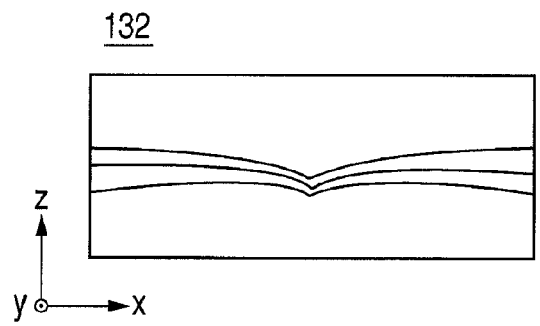

Further, when the electric stage 117-1 is used to repeat the same operation while varying the optical path length of the reference beam path, a two-dimensional distribution of the intensity of the return beam 108 at an XZ plane is obtained, and hence is the tomographic image 132 (FIG. 3C).

As described above, the tomographic image 132 is obtained by arranging the intensity of the return beam 108 from the retina 127 in an array form and displayed by, for example, applying the intensity of the return beam 108 to the gray scale. However, only the boundary thereof is displayed herein.

Example 2

Optical Fiber

In Example 2, an exemplary construction in which any of the optical paths shown in Example 1 is constructed by an optical fiber is described.

Figure 4:
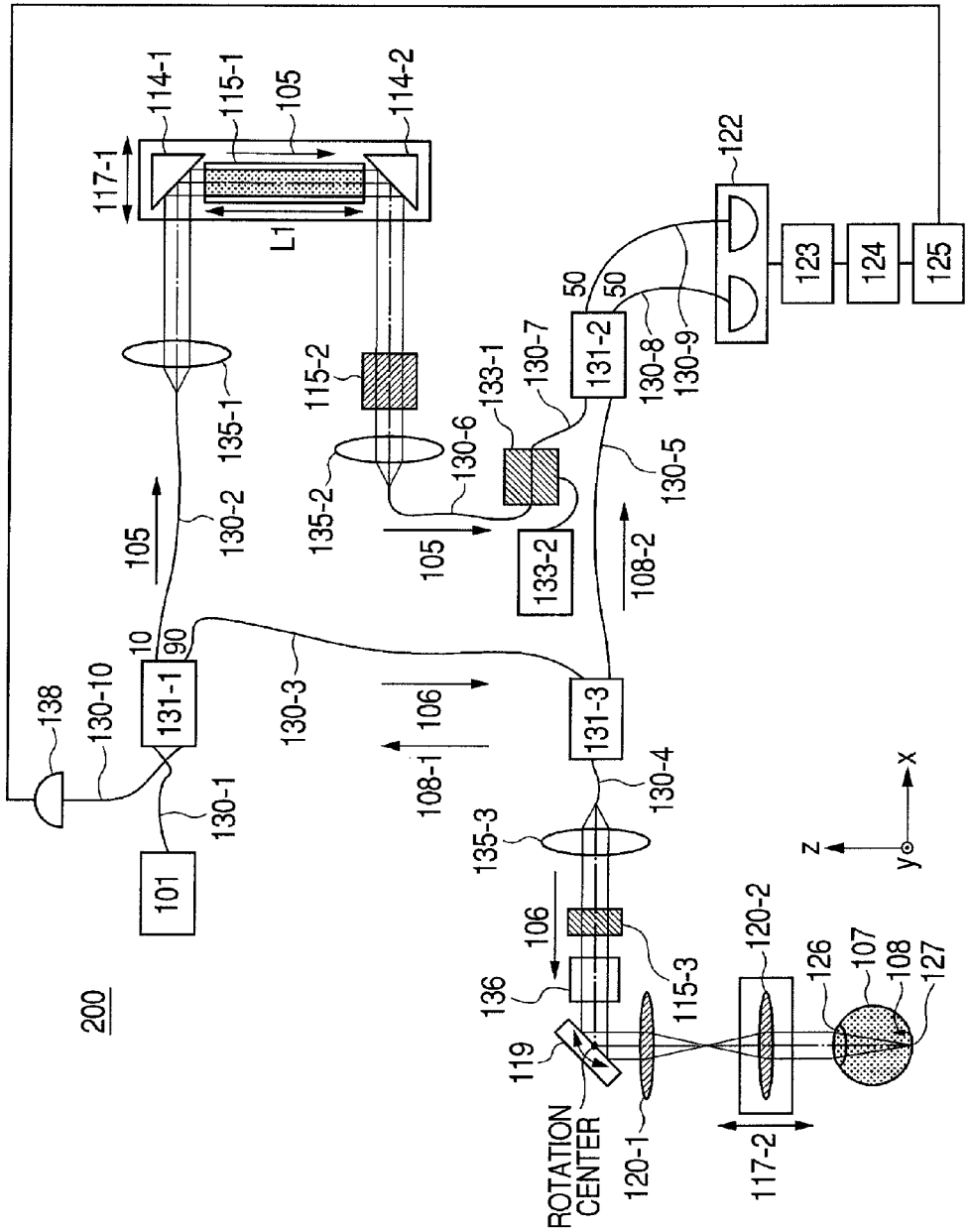
FIG. 4 illustrates the schematic construction of the whole optical system of an OCT apparatus in Example 2 of the present invention.

FIG. 4 illustrates the schematic construction of the whole optical system of an OCT apparatus in this Example. In FIG. 4, the same or corresponding elements to those of Example 1 illustrated in FIG. 1 are given the same reference sign, and so the description of the redundant elements is omitted.

The OCT apparatus 200 illustrated in FIG. 4 is constructed by single mode fibers 130-1 to 130-10, photocouplers 131-1 to 131-3 and the like.

In this Example, the OCT apparatus 200 is used as an apparatus for acquiring a tomographic image of the retina 127 of an eye 107 in an eye to be inspected. In this Example, a part of the optical system is constructed by using the optical fibers, thereby miniaturizing the apparatus.

The apparatus has a fundamental construction that does not differ from that in Example 1 except that the optical fibers are used.

The construction of the optical system in the OCT apparatus of this Example will now be described.

First of all, the construction of the OCT apparatus 200 is roughly described.

As illustrated in FIG. 4, the OCT apparatus 200 of this Example forms a Mach-Zehnder interference system as a whole.

In FIG. 4, the measuring beam 106 is returned as the return beam 108-2 reflected or scattered by the eye 107 that is an object of observation and then combined with the reference beam 105 by the photocoupler 131-2.

After the reference beam 105 and return beam 108-2 are combined and split, the combined beam caused to be incident on the balanced detector 122.

A tomographic image of the eye 107 is formed by using the beam intensity obtained by the balanced detector 122.

The light source 101 will now be described.

The light source 101 itself is the same as in Example 1. The light outputted from the light source 101 is guided to the photocoupler 131-1 through the single mode fiber 130-1 and split at an intensity ratio of 90:10 into the measuring beam 106 and the reference beam 105, respectively.

The optical path of the reference beam 105 will now be described.

The reference beam 105 split by the photocoupler 131-1 is then guided to a lens 135-1 through the single mode fiber 130-2 and adjusted so as to give a parallel beam having a beam diameter of 4 mm.

The electric stage 117-1, the lenses 114-1 and 114-2 attached thereto, and the dispersion compensation glass 115-1 are the same as in Example 1, and so their description is omitted.

The reference beam 105 passes through the dispersion compensation glass 115-2 and then is guided to the single mode fiber 130-6 using a lens 135-2.

The reference beam 105 is further caused to be incident on the photocoupler 131-2 through an acoustooptic modulator 133-1 and the single mode fiber 130-7.

The acoustooptic modulator 133-1 is used for the optical fiber and can conduct frequency shift of 1 MHz using a controller 133-2.

Accordingly, the reference beam 105 obtained herein is the same as in Example 1.

The optical path of the measuring beam 106 will now be described.

The measuring beam 106 split by the photocoupler 131-1 is caused to be incident on the photocoupler 131-3 through the single mode fiber 130-3, and then guided to a lens 135-3 through the single mode fiber 130-4 and adjusted so as to give a parallel beam having a beam diameter of 4 mm.

The measuring beam further passes through the dispersion compensation glass 115-3 and the variable beam expander 136 and then is caused to be incident on the mirror of the XY scanner 119. An optical system between the XY scanner 119 and the eye 107 is the same as in Example 1, and so the description thereof is omitted.

Here, the dispersion compensation glass 115-3 compensates dispersion of the acoustooptic modulator 133-1.

The measuring beam 106 goes to and comes back from the dispersion compensation glass 115-3 herein, so that the thickness of the dispersion compensation glass 115-3 is a half of the thickness of the glass in the acoustooptic modulator 133-1. When the measuring beam 106 is incident on the eye 107, it becomes the return beam 108 by reflection or scattering from the retina 127.

The return beam 108 is further guided to the photocoupler 131-2 through the photocoupler 131-3.

The construction of the measuring system in the OCT apparatus in this Example will now be described.

The OCT apparatus 200 can acquire a tomographic image (OCT image) formed from the intensity of interference signals by the Mach-Zehnder interference system.

The measuring system thereof is described. The return beam 108-2, one return beam of the return beam 108 that is a beam reflected or scattered by the retina 127, is combined with the reference beam 105 by the photocoupler 131-2 and further split to 50:50.

The split beams are then guided to the balanced detector 122 through the single mode fibers 130-8 and 130-9.

The intensity of the combined beam of the reference beam 105 and the return beam 108-2 is converted to voltage.

The resultant voltage signal is amplified by the amplifier 123, a necessary frequency component is taken out through the filter 124, and demodulation and data processing are conducted by the personal computer 125 to form a tomographic image.

The other return beam 108-1 of the return beam 108 described above passes through the photocoupler 131-1 and is guided to the detector 138 through the optical fiber 130-10.

The detector 138 is electrically connected to the personal computer 125 like the interference signal to enables recording and displaying the intensity of the return beam 108-1. The signal obtained by the detector 138 is an intensity signal of the return beam 108-1 by the reflection or scattering on the retina 127, and this signal does not have depth resolution unlike the interference signal.

The method for acquiring a tomographic image using the OCT apparatus of this Example will now be described.

The OCT apparatus 200 is capable of acquiring a tomographic image of a desired site of the retina 127 by controlling two electric stages 117-1 and 117-2 and the XY scanner 119. Details of the method for acquiring the tomographic image are the same as in Example 1, and so the description thereof is omitted.

The adjusting method before acquiring the tomographic image, which is a feature of the present invention, is also the same as in Example 1, and so the description thereof is omitted.

Example 3

Beam Diameter Adjustment Based on Pupil Diameter

In this Example, after the adjusting method before acquiring the tomographic image in Example 1 or 2 in the construction of the OCT apparatus in Example 1 or 2 is conducted, a beam diameter is adjusted and measured at the time of taking a tomographic image. A tomographic image having high contract can be thereby acquired regardless of the optical characteristics (mainly, aberration such as astigmatism) of individual eyes to be inspected.

Figure 6B:
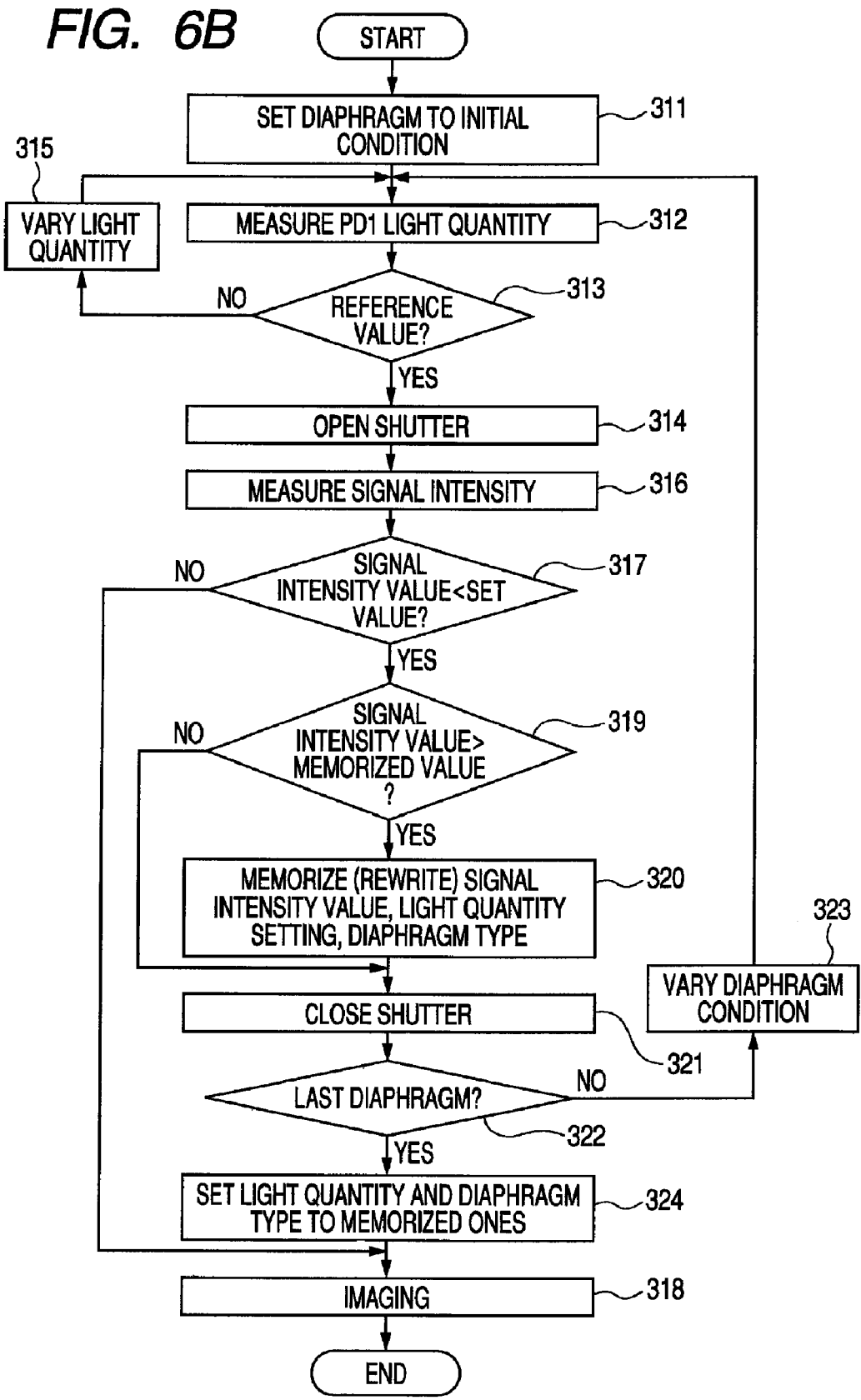

This Example is described with reference to FIG. 6A. FIG. 6A is a flow diagram illustrating adjustment of a beam diameter. In the adjusting method of this Example, the following steps may be continuously conducted. However, the present invention is not limited thereto. Alternatively, it may be so constructed that the following steps are automatically conducted by using a computer.

First, in a first step, the variable beam expander 136 as a beam adjusting unit is adjusted to adjust the beam diameter of the measuring beam 106 to the pupil diameter of an eye to be inspected (Step 301). Here, the beam diameter of the measuring beam 106 is determined so as to be the same as or smaller than the pupil diameter. It is hence necessary to acquire signal intensity at the moment when the beam diameter of the measuring beam 106 conforms to the pupil diameter for determining the beam diameter of the measuring beam 106. Thus, it is not necessary to completely fit the beam diameter to the pupil diameter, and it is only necessary to adjust the beam diameter equally to or larger than the pupil diameter (Step 302). It is thereby possible to acquire the signal intensity at the moment when the beam diameter of the measuring beam 106 conforms to the pupil diameter. The beam diameter may be adjusted by measuring the pupil diameter in advance and fitting the beam diameter to that diameter. Alternatively, the pupil and the beam diameter are monitored upon measurement to adjust the beam diameter such that the beam diameter is equal to or larger than the pupil diameter. For example, when the pupil diameter of an eye to be inspected is 5 mm, the beam diameter of the measuring beam can be selected to be 5 mm, 5.5 mm or the like. When the pupil diameter of an eye to be inspected is 6 mm, the beam diameter of the measuring beam can be selected to be 6 mm, 6.5 mm or the like.

The return beam 108-1 that has been caused to be incident on the eye to be inspected and reflected or scattered by the retina 127 is caused to optically interfere with the reference beam 105, and the signal intensity thereof is detected by the balanced detector 122 (Step 303). The signal intensity is a time average value of signal intensities acquired with a single beam diameter.

The beam diameter is gradually decreased from the pupil diameter or a diameter larger than the pupil diameter (Step 304) to detect the signal intensity of a coherent beam by the balanced detector 122 (Step 305). At that time, the signal intensity may also be displayed as a graph or a two-dimensional image (Step 306), since it is information depending on the beam diameter.

Then, in a second step, a beam diameter with maximum signal intensity is found from the information of the beam diameter and signal intensity, which has been acquired in the first step (Step 307).

Then, in a third step, the variable beam expander 136 is adjusted so as to give the beam diameter found in the second step. At that time, the beam diameter is not limited to the beam diameter at which the signal intensity becomes maximum, and it is only necessary for the beam diameter to fall within a region in the vicinity of the point where the signal intensity becomes maximum, and in which the same effect is achieved.

The method for acquiring a tomographic image using the OCT apparatus of this Example overlaps with the method described in Example 1, and so the description thereof is omitted.

Example 4

Beam Condition Varying Portion

In Example 4, measurement is conducted by adjusting not only the beam diameter but also the beam form and the position of a beam passing through above the pupil of an eye to be inspected compared with Example 3.

The construction of the OCT apparatus, and the adjusting method before acquisition are the same as in Examples 1, 2 and 3, and so the description thereof is omitted.

In this Example, however, an aperture varying device is provided as a beam condition varying portion in place of the variable beam expander 136 in FIGS. 1, 2A and 2C.

Figure 8A:
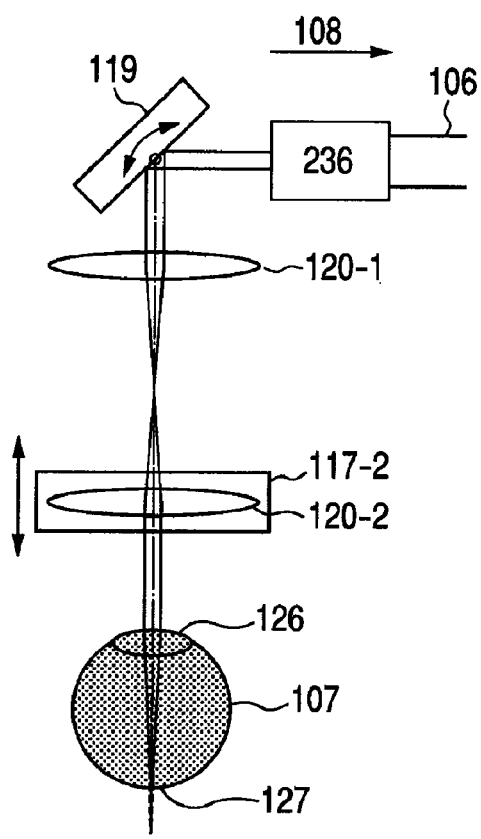
FIGS. 8A, 8B and 8C illustrate an aperture varying device in Example 4 of the present invention.

In FIG. 8A, the aperture varying device (beam condition varying portion) 236 is arranged at the position of the beam expander that is the beam adjusting unit in Example 1 or 2.

The aperture varying device in this Example is described with reference to FIGS. 8A to 8C.

Figure 8B:
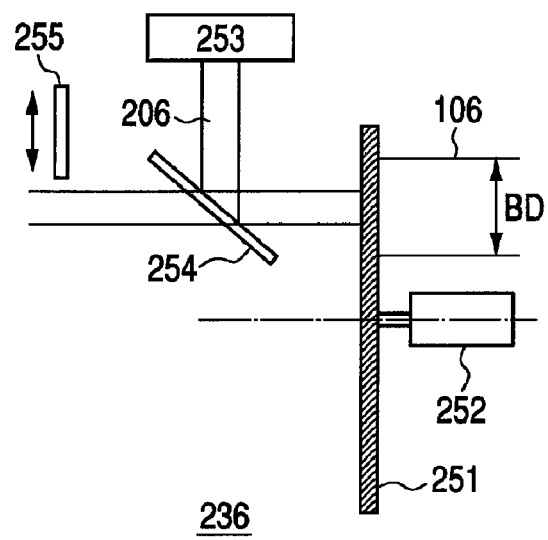

In FIG. 8B, are illustrated the aperture varying device 236, a disc 251 having a plurality of apertures, a stepping motor 252 for rotating the disc 251 to vary an aperture positioned on an optical path 106, a photo detector 253 for detecting the light quantity of a beam after passing through the aperture, a half mirror 254 for guiding a part of the beam after passing through the aperture to the photo detector 253, and a shutter 255 movable in the directions of the arrow so as to suitably shut off the beam going toward an eye to be inspected.

Figure 8C:
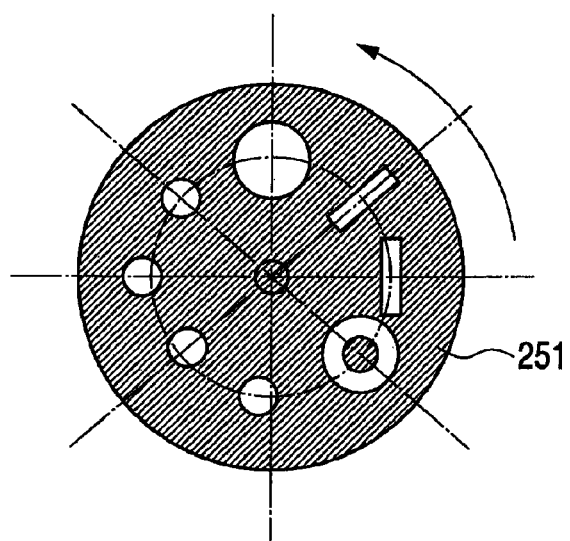

As illustrated in FIG. 8C, openings that are apertures provided in the disc 251 at equal distances from the center and at equal intervals are so formed that an aperture can be selected by rotating the disc in the direction of the arrow in the drawing. Incidentally, the types and arrangements of the apertures in FIG. 8C are typical ones, and they are not limited thereto. Although the disc form has been described, such a constitution that selection can be made by sliding movement is also applicable. Moreover, when the number of the apertures is small, such a constitution that a member for controlling an aperture with respect to a reference aperture can be provided and removed is also applicable.

A light quantity passing through an aperture varies according to a difference in opening area for the respective apertures, and a light quantity outputted from the light source 101 is suitably adjusted according to the aperture based on the light quantity detected in the photo detector 253. Alternatively, a concentration filter, which can adjust the light quantity, is inserted into an optical path arriving at the eye to be inspected, and the concentration filter is adjusted to make constant the light quantity of the beam going toward the eye to be inspected.

The apertures provided in the aperture varying device are described with reference to FIGS. 9A to 9L. In each drawing, a broken line BD indicates a beam diameter before passing through the aperture, and an AP indicated by a blank area is an opening and indicates that a beam passes through the blank area.

Figure 9A:
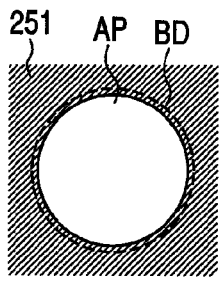
FIGS. 9A, 9B, 9C, 9D, 9E, 9F, 9G, 9H, 9I, 9J, 9K and 9L illustrate examples of an aperture in Example 4 of the present invention.
Figure 9B:
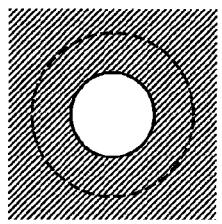

The apertures illustrated in FIGS. 9A and 9B vary the size of a beam diameter and have the same effect as in Example 3. The diameters of the apertures were set to 4 mm for FIG. 9A and 2 mm for FIG. 9B.

Figure 9C:
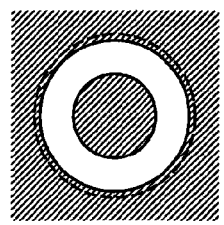
Figure 9D:
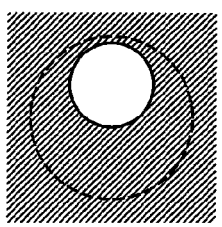
Figure 9E:
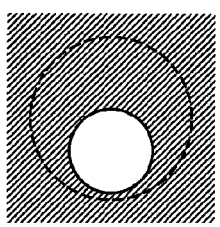
Figure 9F:
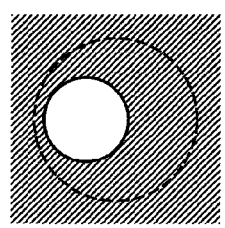
Figure 9G:
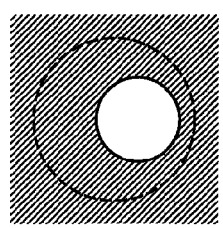
Figure 9H:
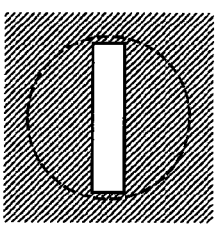
Figure 9I:
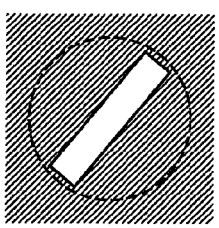
Figure 9J:
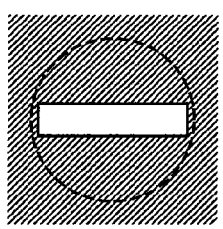
Figure 9K:
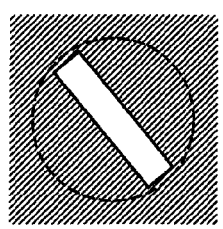

The aperture illustrated in FIG. 9C is a ring aperture adapted for causing only a outer peripheral portion of a beam to pass through, and imaging may be well conducted in some cases compared with FIG. 9B when spherical aberration is present in an eye to be inspected. This ring was set to 4 mm in outer diameter and 2 mm in inner diameter.

The apertures illustrated in FIGS. 9D to 9G are adapted for varying a position of a beam passing through on the pupil of an eye to be inspected. This is effective for an eye to be inspected whose transmittance is partially varied, such as cataract, in addition to the aberration of the eye. For example, when the transmittance of only a central part is poor, the ring aperture in FIG. 9C shuts off a center of a measuring beam, and the measuring beam passes through the peripheral part relatively good in transmittance, whereby the measuring beam arrives at the eyeground, and at the same time reflection on the part poor in transmittance is inhibited, and so it can be prevented that stray beam enters the return beam. When the part poor in transmittance is present at another position asymmetric to an optical axis than a center, the apertures in FIGS. 9D to 9G are successively varied, whereby a part good in transmittance can be irradiated with the measuring beam. The opening diameter in each of FIGS. 9D to 9G was set to 2 mm.

The apertures illustrated in FIGS. 9H to 9K are apertures having a slit form and effective in the case where an eye to be inspected has astigmatism. The reason why the angle of the slit is varied is that the slit is fitted to the direction of astigmatism. This slit form was set to 4 mm in length and 1 mm in width.

Figure 9L:
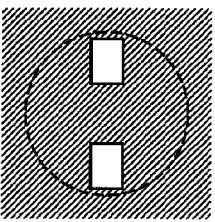

The aperture illustrated in FIG. 9L is an aperture having a combined opening of a slit and a ring and effective for an eye to be inspected having astigmatism and spherical aberration. The aperture whose angle is varied is the same as in FIGS. 9H to 9K, and so the illustration thereof is omitted.

The above-described apertures are mere examples, and the aperture varying device may be equipped with more kinds of apertures. For example, it is favorable that the type of the opening for adjusting the size of the beam diameter is increased, and a circular opening having a diameter of 1 mm is provided. It is also favorable that the radial position of the ring aperture and the type of the opening width of the slit are increased.

The best aperture is selected from among the above-described apertures according to the eye to be inspected to conduct imaging. A process therefor is described with reference to FIG. 6B.

First, the aperture varying device 236 is set to an initial condition (Step 311). Specifically, it is set to the circular large aperture of FIG. 9C. The shutter 255 is kept in a state where a beam is shut off so as not to go toward the eye to be inspected.

Then, a light quantity after passed through the aperture is by the photo detector 253 (described as PD1 in FIG. 6B) (Step 312). Whether it is a reference value or not is determined (Step 313). When the light quantity is of the reference value, the shutter is opened to guide the beam to the eye to be inspected. When the light quantity is out of the reference value, the above-described light quantity adjustment is conducted (Step 315).

Then, the beam is caused to be incident on the eye to be inspected, a return beam 108-1 reflected or scattered on the retina 127 is caused to optically interfere with a reference beam 105, and the signal intensity thereof is detected by the balanced detector 122 (Step 316). Whether the signal intensity effective for imaging is not lower than the set value or not is determined (Step 317). When the signal intensity value is not smaller than the set value, an imaging step is conducted (Step 318). When the signal intensity value is smaller than the set value, whether the signal intensity value is larger than the memorized value or not is determined (Step 319).

Here, the memorized value is zero in the initial condition. When the measured value of the signal intensity is larger than the memorized value, the signal intensity at this time is regarded as a memorized value to memorize or rewrite the light quantity setting and the aperture type (Step 320). With respect to the aperture type, the rotational angle of the disc 251 may be memorized. When the measured value of the signal intensity is not larger than the memorized value, the shutter is closed without going though Step 320 to shut off the beam going toward the eye to be inspected (Step 321).

Then, whether the aperture is varied to the last type or not is confirmed (Step 322). When an aperture to be selected is left, the stepping motor 252 is caused to rotate so as to select the next aperture (Step 323). Then, going back to Step 312 to measure PD1 light quantity, the process is repeated. When the aperture is varied to the last type, the light quantity and the aperture type are set to memorized ones (Step 324).

When a signal intensity not less than the set value is obtained by going through the above-described process, imaging can be conducted with the aperture at that time. When it is less than the set value, imaging can be conducted by setting the aperture and the light quantity to those with a maximum signal intensity. In other words, a tomographic image of an eyeground of an eye to be inspected can be obtained in the best condition according to the condition of the eye to be inspected.

The method for acquiring a tomographic image using the OCT apparatus in this Example overlaps with the method described in Example 1, and so the description thereof is omitted. Although this Example has been described as the apparatus having the step of automatically selecting the aperture, it may be so constructed that the aperture can be freely varied by displaying the signal intensity to an inspector by an indicator on a screen. It is not always necessary to vary all apertures to all subjects. When the condition of an eye to be inspected has been known in advance (for example, the condition of astigmatism has been discovered), apertures to be varied are limited, whereby the time required of imaging may be shortened. Although such a construction that the apertures are arranged on the disc to select them by rotating the disc has been described, such a construction that separately provided apertures are selected and inserted into an optical path, thereby varying the aperture may also be employed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2008-122633, filed May 8, 2008, and No. 2009-109393, filed Apr. 28, 2009, which are hereby incorporated by reference herein in their entirety.

The invention claimed is:

1. An optical coherence tomographic imaging apparatus, in which light from a light source is split into a measuring beam and a reference beam, and a return beam of the measuring beam reflected or scattered by an object and the reference beam are used to image a tomographic image of the object, the apparatus comprising:
    a first detection unit that detects a first return beam, wherein the first return beam corresponds to the measuring beam with a first beam diameter;
    an adjusting unit that adjusts a focusing position of the measuring beam on the object with the first beam diameter based on the detected first return beam;
    a beam diameter varying unit that varies the first beam diameter to a second beam diameter which is larger than the first beam diameter; and
    a second detection unit that detects a combined beam obtained by combining a second return beam with the reference beam,
    wherein the second return beam corresponds to the measuring beam with the second beam diameter.

2. The optical coherence tomographic imaging apparatus according to claim 1, further comprising a return beam splitting unit that splits the return beam to travel along an optical path of the first detection unit and an optical path of the second detection unit.

3. The optical coherence tomographic imaging apparatus according to claim 1, further comprising a recording unit that reports that the first return beam or the second return beam does not have an intensity necessary to be detected by said first detection unit or said second detection unit.

4. The optical coherence tomographic imaging apparatus according to claim 1, wherein at least one optical path of a first optical path guiding the light from the light source to an optical path at which the light is split into the measuring beam and the reference beam, a second optical path guiding the measuring beam to the object, and a third optical path guiding the reference beam to a reference mirror, is constructed by an optical fiber.

5. The optical coherence tomographic imaging apparatus according to claim 1, further comprising an optical path length adjustment unit that adjusts a difference between an optical path length of the measuring beam and an optical path length of the reference beam based on the first return beam after the adjusting unit adjusts the focusing position, and a tomographic image acquisition unit that acquires the tomographic image based on the combined beam obtained by combining the second return beam with the reference beam after the optical path length adjustment unit adjusts the difference.

6. The optical coherence tomographic imaging apparatus according to claim 5, wherein the optical path length adjustment unit adjusts the difference based on the second return beam after adjusting the difference based on the first return beam.

7. The optical coherence tomographic imaging apparatus according to claim 1, further comprising a beam condition varying portion that varies a beam condition of the measuring beam, wherein the beam condition which is varied is the second beam diameter,
whereby an intensity of the second return beam is detected for every beam condition varied by the beam condition varying portion, and the combined beam obtained by using the measuring beam having the beam condition is selected based on the detected intensity.

8. The optical coherence tomographic imaging apparatus according to claim 7, wherein the beam condition is at least one of a form and a position in a plane which is perpendicular to an optical axis direction of the measuring beam.

9. The optical coherence tomographic imaging apparatus according to claim 7, wherein said beam condition varying portion comprises a plurality of lenses that form the beam condition of the measuring beam by incidence of the measuring beam and is so constructed that the beam condition is varied by causing the measuring beam to be incident on different lenses.

10. The optical coherence tomographic imaging apparatus according to claim 7, wherein said beam condition varying portion comprises a disc arranged perpendicularly to the optical axis direction and a plurality of openings provided in the disc and is so constructed that the measuring beam is selectively incident on any of the plurality of openings by rotating the disc.

11. The optical coherence tomographic imaging apparatus according to claim 1, wherein the beam diameter varying unit varies the first beam diameter to the second beam diameter after the adjusting unit adjusts the focusing position.

12. The optical coherence tomographic imaging apparatus according to claim 1, wherein the beam diameter varying unit varies the second beam diameter to a third beam diameter which is smaller than the second beam diameter such that an intensity of the second return beam is a predetermined intensity or higher.

13. The optical coherence tomographic imaging apparatus according to claim 1, wherein after the adjusting unit adjusts the focusing position based on the first return beam, the adjusting unit adjusts a focusing position of the measuring beam on the object with the second beam diameter based on the second return beam.

14. The optical coherence tomographic imaging apparatus according to claim 1, wherein the object is an eye.

15. An optical coherence tomographic imaging method in an optical coherence tomographic imaging apparatus, in which light from a light source is split into a measuring beam and a reference beam, and a return beam of the measuring beam reflected or scattered by an object and the reference beam are used to image a tomographic image of the object, the method comprising the steps of:

detecting, by a first detection unit, a first return beam corresponding to the measuring beam with a first beam diameter;
adjusting, by an adjusting unit, a focusing unit for focusing the measuring beam on the object with the first beam diameter based on the detected first return beam;
varying the first beam diameter to a second beam diameter which is larger than the first beam diameter using a beam diameter varying unit; and
detecting, by a second detection unit, a combined beam obtained by combining a second return beam with the reference beam,
wherein the second return beam corresponds to the measuring beam with the second beam diameter.

16. The optical coherence tomographic imaging method according to claim 15, wherein said second-detection-unit detecting step includes a step of recording the position of the optical path length of the reference beam adjusted by an optical path length adjusting unit, and wherein in the combined-beam detecting step the optical path length of the reference beam is adjusted by using a recorded position of the optical path length adjusted by the optical path length adjusting unit as a reference.

17. A non-transitory storage medium readable by a computer, storing a program for performing the optical coherence tomographic imaging method according to claim 15 with the computer.

18. The optical coherence tomographic imaging method according to claim 15, wherein the beam diameter varying unit varies the first beam diameter to the second beam diameter after the focusing position is adjusted.

19. An imaging apparatus that acquires an image of an object based on a return beam from the object irradiated with a measuring beam, the imaging apparatus comprising:
an adjusting unit that adjusts a focusing position of a measuring beam on the object with a first beam diameter based on a first return beam that corresponds to the measuring beam with the first beam diameter; and
a detection unit that detects a second return beam that corresponds to a measuring beam with a second beam diameter larger than the first beam diameter after the adjusting unit adjusts the focusing position.

20. The imaging apparatus according to claim 19, wherein the adjusting unit adjusts the focusing position of the measuring beam so as to increase an intensity of the detected second return beam.

21. The imaging apparatus according to claim 20, further comprising an acquisition unit that acquires a tomographic image of the object based on a combined beam obtained by combining the return beam from the object irradiated with the measuring beam and a reference beam that corresponds to the measuring beam, and
wherein the tomographic image of the object is obtained by using the measuring beam with a beam diameter varied by a beam diameter varying unit.

22. The imaging apparatus according to claim 19, further comprising:
a varying unit that varies a beam condition of the measuring beam based on optical characteristics of the eye.

23. The imaging apparatus according to claim 22, wherein the varying unit comprises a beam diameter varying unit that varies a size of a beam diameter of the measuring beam so as to increase an intensity of the detected second return beam.

24. The imaging apparatus according to claim 22, wherein the varying unit comprises a beam diameter varying unit that varies at least one of a form of the measuring beam and a beam irradiation position of the object so as to increase an intensity of the detected second return beam.

25. The imaging apparatus according to claim 22, further comprising an acquisition unit that acquires a tomographic image of the object based on a combined beam obtained by combining the return beam from the object irradiated with the measuring beam and a reference beam that corresponds to the measuring beam, wherein the tomographic image of the object is acquired by using the measuring beam with the beam condition varied by the varying unit.

26. The imaging apparatus according to claim 19, wherein after the adjusting unit adjusts the focusing position based on the first return beam, the adjusting unit adjusts a focusing position of the measuring beam on the object with the second beam diameter based on the second return beam.

27. The imaging apparatus according to claim 19, further comprising an optical path length adjustment unit that adjusts a difference between an optical path length of the measuring beam and an optical path length of a reference beam based on the first return beam after the adjusting unit adjusts the focusing position, and a tomographic image acquisition unit that acquires a tomographic image based on the combined beam obtained by combining the second return beam with the reference beam after the optical path length adjustment unit adjusts the difference.

28. The imaging apparatus according to claim 27, wherein the optical path length adjustment unit adjusts the difference based on the second return beam after adjusting the difference based on the first return beam.

29. An imaging apparatus that acquires an image of an object based on a combined beam obtained by combining a return beam from the object irradiated with a measuring beam with a reference beam that corresponds to the measuring beam, the imaging apparatus comprising:
  an optical path length adjustment unit that adjusts a difference between an optical path length of the measuring beam and an optical path length of the reference beam based on a first return beam that corresponds to a measuring beam with a first beam diameter; and
  a detection unit that detects a combined beam obtained by combining a second return beam that corresponds to a measuring beam with a second beam diameter larger than the first beam diameter with the reference beam after the optical path length adjustment unit adjusts the difference.

30. The imaging apparatus according to claim 29, further comprising an acquisition unit that acquires a tomographic image of the object with the optical path length difference varied by the adjusting unit based on the combined beam obtained by combining the return beam from the object irradiated with the measuring beam and the reference beam that corresponds to the measuring beam, wherein the optical path length adjustment unit adjusts the difference based on the second return beam after adjusting the difference based on the first return beam.

31. An imaging method for acquiring an image of an object based on a return beam from the object irradiated with a measuring beam, the method comprising the steps of:
  adjusting a focusing position of a measuring beam on the object with a first beam diameter based on a first return beam that corresponds to the measuring beam with the first beam diameter; and
  detecting a second return beam that corresponds to a measuring beam with a second beam diameter larger than the first beam diameter after the focusing position is adjusted.

32. The imaging method according to claim 31, further comprising the step of adjusting a focusing position of the measuring beam on the object with the second beam diameter based on the second return beam.

33. The imaging method according to claim 31, further comprising the step of adjusting a difference between an optical path length of the measuring beam and an optical path length of a reference beam based on the first return beam after the focusing position is adjusted, and acquiring the image based on a combined beam obtained by combining the second return beam with the reference beam after the difference is adjusted.

34. A non-transitory storage medium storing a program that causes an apparatus to carry out a method according to claim 31.

35. An imaging method for acquiring an image of an object based on a combined beam obtained by combining a return beam from the object irradiated with a measuring beam with a reference beam that corresponds to the measuring beam, the method comprising the steps of:
  adjusting a difference between an optical path length of the measuring beam and an optical path length of the reference beam based on a first return beam that corresponds to a measuring beam with a first beam diameter; and
  detecting a combined beam obtained by combining a second return beam that corresponds to a measuring beam with a second beam diameter larger than the first beam diameter with the reference beam after the difference is adjusted.

36. The imaging method according to claim 35, further comprising the step of adjusting the difference based on the second return beam after the difference is adjusted based on the first return beam.

37. A non-transitory storage medium storing a program that causes an apparatus to carry out a method according to claim 35.

* * * * *